United States Patent [19]

Castelijns et al.

[11] Patent Number: 5,319,125

[45] Date of Patent: Jun. 7, 1994

[54] METHOD FOR THE PREPARATION OF 2-(2-CYANOETHYL)-CYCLOPENTANONES

[75] Inventors: Anna M. C. F. Castelijns; Hubertus J. A. Dielemans, both of Beek, Netherlands

[73] Assignee: DSM, N.V., Heerlen, Netherlands

[21] Appl. No.: 39,745

[22] Filed: Mar. 30, 1993

[30] Foreign Application Priority Data

Mar. 30, 1992 [NL] Netherlands .......................... 9200580

[51] Int. Cl.$^5$ ........................................... C07C 253/30
[52] U.S. Cl. .................................................. 558/368
[58] Field of Search ........................................ 558/368

[56] References Cited

U.S. PATENT DOCUMENTS 4,267,362 5/1981 Meyer et al. .................. 558/368 X

FOREIGN PATENT DOCUMENTS 815262 6/1959 United Kingdom ................. 558/368

OTHER PUBLICATIONS

Chemical Abstracts, vol. 75, (1971) Abstract No. 19354p, "Monocyanoethylation of Ketones in the Presence of Primary Amine and Carboxylic Acid", Niehimura, et al.

*Primary Examiner*—Joseph Paul Brust
*Attorney, Agent, or Firm*—Cushman, Darby & Cushman

[57] ABSTRACT

The invention relates to a method for the preparation of a 2-(2-cyanoethyl)-cyclopentanone by reaction of a cyclopentanone which contains at least one α-H atom with an α,β-unsaturated nitrile in the presence of a catalytic amount of pyrrolidine as catalyst and optionally also a catalytic amount of an acid compound. A high selectivity and a high catalyst activity are achieved with the method.

10 Claims, No Drawings

METHOD FOR THE PREPARATION OF 2-(2-CYANOETHYL)-CYCLOPENTANONES

The invention relates to a method for the preparation of a 2-(2-cyanoethyl)-cyclopentanone by reaction of a cyclopentanone which contains at least one $\alpha$-H atom with an $\alpha,\beta$-unsaturated nitrile, in the presence of a catalytic amount of amine.

A method of this type is disclosed in U.S. Pat. No. 2,850,519, wherein, for example, cyclopentanone is reacted with acrylonitrile in the presence of a primary amine, cyclohexylamine and acetic acid as catalyst. In practice, a method of this type is found to be associated with a relatively low selectivity and a relatively low production capacity. Moreover, in reactions of this type an increase in the selectivity is frequently accompanied by a reduction in the production capacity.

The aim of the invention is to provide a method with which the said reaction takes place with higher selectivity and with which, at the same time, a higher production capacity than was hitherto the case is achieved.

This is achieved according to the invention by using pyrrolidine as catalyst.

It has been found that when cyclopentanone was used as the starting material in combination with pyrrolidine as catalyst both a higher selectivity and a higher catalyst activity, resulting in a higher production capacity, were achieved. When a similar method was carried out using other ketones, such as cyclohexanone, poorer results were obtained compared with the results obtained using a primary amine as catalyst. In addition, it was found that when secondary amines other than pyrrolidine were used as the catalyst under comparable reaction conditions, no yield or a very much poorer yield was produced using cyclopentanone as the starting material.

The 2-(2-cyanoethyl)-cyclopentanone obtained by reaction of cyclopentanone and acrylonitrile is, for example, an intermediate in the preparation of 2,3-cyclopentenopyridine. In order to prepare 2,3-cyclopentenopyridine, for example, the 2-(2-cyanoethyl)-cyclopentanone obtained by the method according to the invention is converted to 2,3-cyclopentenopyridine in a 2-step process, catalytic hydrogenation of the 2-(2-cyanoethyl)cyclopentanone first being carried out in the liquid phase to give 2,3-cyclopentanopiperidine, followed by catalytic dehydrogenation of the 2,3-cyclopentanopiperidine obtained, as described in J. Am. Chem. Soc. 82 469 (1960). Another possible route is the direct catalytic gas phase cyclisation and dehydrogenation of 2-(2-cyanoethyl)-cyclopentanone, as described, for example, in GB-A-1304155.

When the method according to the invention is used a higher selectivity can be achieved both in respect of the cyclopentanone and in respect of the $\alpha,\beta$-unsaturated nitrile. Pyrrolidine, as the catalyst, also shows a higher activity, so that a higher production capacity can be achieved.

The cyclopentanone can optionally be substituted in one or more locations in the nucleus, for example by an alkyl group having 1-10 C atoms.

The $\alpha,\beta$-unsaturated nitrile used can be, for example, acrylonitrile and homologues thereof, such as methacrylonitrile and crotononitrile.

The ratio between the amount of cyclopentanone and $\alpha,\beta$-unsaturated nitrile which is used in the method according to the invention can be varied. Theoretically, one mol of cyclopentanone is needed per mol of $\alpha,\beta$-unsaturated nitrile. In practice, an excess of ketone is used in order to obtain a high selectivity. Usually, the molar ratio of cyclopentanone to $\alpha,\beta$-unsaturated nitrile will be between 1 and 5. In the method according to the invention a high selectivity can be achieved using a molar ratio of cyclopentanone to $\alpha,\beta$-unsaturated nitrile of between 1.5 and 3.

The amount of pyrrolidine which is used is not critical and is usually between 0.05 and 0.2 mol per mol of $\alpha,\beta$-unsaturated nitrile.

If a small amount of an acid compound is present in addition to pyrrolidine, this usually results in an improvement in the selectivity. Suitable acid compounds are, for example, acetic acid, benzoic acid, caproic acid, hydrochloric acid, phosphoric acid and sulphuric acid. Preferably, an acid is used which is easy to remove by distillation, such as, for example, acetic acid. Moreover, the use of acetic acid, compared with, for example, benzoic acid, has the additional advantage that a higher activity is achieved. Usually 0.01-0.2 mol of acid compound is used per mol of pyrrolidine.

The method according to the invention is usually carried out at a temperature between 50° C. and 200° C., preferably between 80° C. and 150° C. The lower the temperature chosen, the longer will be the reaction time needed to achieve a given conversion, which has an adverse influence on the production capacity.

The pressure under which the reaction according to the invention is carried out is not critical. Usually a pressure is chosen which is between the vapour pressure prevailing at the reaction temperature and 10 MPa. The pressure is so chosen that the reaction, which may or may not be carried out in the presence of a solvent or dispersing agent, can take place in the liquid phase. Preferably, the reaction is carried out under a pressure of between 0.1 and 2 MPa.

The 2-(2-cyanoethyl)-cyclopentanone can be obtained from the reaction mixture in high purity by distillation without, as is the case when primary amines are used, extra washings being necessary.

The invention will be further illustrated with the aid of the following examples, without, however, being restricted thereto.

DEFINITIONS $\alpha$: molar ratio of ketone to nitrile
$\beta$: molar ratio of nitrile to amine
$\gamma$: molar ratio of amine to acid

EXAMPLE I

Preparation of 2-(2-cyanoethyl)cyclopentanone 3024 grams of cyclopentanone (36 mols), 954 grams of acrylonitrile (18 mols), 63.9 grams of pyrrolidine (0.9 mol) and 4.2 grams of acetic acid (0.07 mol) were metered successively ($\alpha=2$; $\beta=20$; $\gamma=12.8$) into a reactor which has a capacity of 5 liters and is provided with a stirrer, a thermometer and a condenser. The mixture was then heated under total reflux for 2 hours, with stirring. During this period the temperature rose from 95° C to about 141° C. The reaction mixture was then cooled to room temperature. According to gas chromatographic analysis, the crude reaction mixture contained, inter alia, 21.0 grams of acrylonitrile, 1623.9 grams of cyclopentanone and 2145.4 grams of 2-(2-cyanoethyl)-cyclopentanone. This signifies that 97.8% of the original amount of acrylonitrile had been converted. The selectivity was 89% with respect to converted acrylonitrile and 94% with respect to converted cyclopentanone. The production capacity for crude 2-(2-cyanoethyl)-cyclopentanone was 1.935 mol/(kg.-hour). The crude reaction mixture was then distilled. Under atmospheric conditions, the unconverted acrylonitrile was first removed. The system was then placed under vacuum and further distilled. Under a pressure of 50 mm Hg and a top temperature of 85° C., 1513 grams of distillate which predominantly consisted of cyclopentanone were obtained. The pressure was then reduced to 10 mm Hg. 249 grams of an intermediate fraction were distilled off until a bottom temperature of 185° C. was reached, after which 1945 grams of main fraction, 99.3% of which consisted of 2-(2-cyanoethyl)-cyclopentanone (distillation yield =90%), were obtained until a bottom temperature of 235° C. was reached.

EXAMPLE II

Preparation of 2-(2-cyanoethyl)-cyclopentanone

In a manner analogous to that described in Example I, a mixture consisting of 3024 grams of cyclopentanone (36 mols), 954 grams of acrylonitrile (18 mols), 127.8 grams of pyrrolidine (1.8 mols) and 16.6 grams of benzoic acid (0.136 mol) was heated under total reflux for 2 hours ($\alpha=2$; $\beta=10$; $\gamma=13.23$). During this period the temperature rose from 95° C. to about 138° C. After cooling to room temperature, the mixture, according to gas chromatographic analysis, contained 28.6 grams of acrylonitrile, 1663.2 grams of cyclopentanone and 2033.2 grams of 2-(2-cyanoethyl)-cyclopentanone. This signifies that 97% of the original amount of acrylonitrile had been converted. The yield was 85% with respect to converted acrylonitrile and 91% with respect to converted cyclopentanone. The production capacity for crude 2-(2-cyanoethyl)-cyclopentanone was 1.800 mol/kg.hour.

COMPARATIVE EXPERIMENT A

Preparation of 2-(2-cyanoethyl)-cyclopentanone

In a manner analogous to that described in Example I, a mixture consisting of 3024 grams of cyclopentanone (36 mols), 954 grams of acrylonitrile (18 mols), 238 grams of cyclohexylamine (2.4 mols) and 5.8 grams of benzoic acid (0.047 mol) was heated under total reflux ($\alpha=2$; $\beta=7.5$; $\gamma=51$). After 4½ hours reaction the temperature had risen from 93° C. to 115° C. According to gas chromatographic analysis, the mixture contained, inter alia, 166.0 grams of acrylonitrile, 2162.2 grams of cyclopentanone and 971.3 grams of 2-(2-cyanoethyl)-cyclopentanone. This signifies that 82.6% of the original amount of acrylonitrile had been converted. The yield was 47.7% with respect to converted acrylonitrile and 69.2% with respect to converted cyclopentanone. After the mixture had been heated for a further 3 hours under reflux, the temperature had risen to 130° C. According to gas chromatographic analysis, all acrylonitrile had been converted and the mixture also contained, inter alia, 1814.4 grams of cyclopentanone and 1171.3 grams of 2-(2-cyanoethyl)-cyclopentanone, The yield was 47.5% with respect to converted acrylonitrile and 59.2% with respect to converted cyclopentanone. The production capacity for crude 2-(2-cyanoethyl)-cyclopentanone was 0.270 mole/kg.hour. Direct distillation of the crude reaction mixture, analogously to the method as described in Example I, yielded a main fraction which contained only about 93% of 2-(2-cyanoethyl)-cyclopentanone, at a top temperature of 112°-119° C. and a pressure of 3 mm Hg. The contamination consisted mainly of the Schiffs base of the product with cyclohexylamine. Product of a sufficiently high purity was obtained only by taking up the crude product, after removal of the volatile components by distillation, in toluene and washing with a dilute aqueous acid solution (20% $H_2SO_4$ solution) followed by distillation of the organic phase.

EXAMPLES III AND IV AND COMPARATIVE EXPERIMENTS B, C, D, E AND F

Preparation of 2-(2- cyanoethyl)-cyclopentanone

In the same way as in Example I, the experiments shown in Table 1 were carried out in an autoclave having a capacity of 160 ml. For these experiments, the reaction mixtures were heated under autogenous pressure for the indicated reaction time (t). After this time had elapsed, the reaction mixtures were cooled and analyzed by gas chromatography. The results are shown in Table 1.

Comparative Experiments G to K

In the same was as in Example I, the experiments shown in Table 2 were carried out in a 160 ml autoclave. For these experiments the reaction mixtures were heated under autogenous pressure for the indicated reaction time (t). After this time had elapsed, the reaction mixtures were cooled and analyzed by gas chromatography. The results are shown in Table 2.

TABLE 1

| Experiment No. | Amine | Acid | alfa | beta | gamma | T (°C.) | t (hours) | conv. ACN (%) | sel. ACN (%) | conv. cpton (%) | sel. cpton (%) | prod. cap. (mol/kg/hour) |
|---|---|---|---|---|---|---|---|---|---|---|---|---|
| B | IPA | BzOH | 2 | 5 | 27 | 110 | 2 | 95.1 | 53.9 | 35.3 | 72.6 | 1.097 |
| C | IPA | BzOH | 3 | 5 | 27 | 110 | 2 | 97.6 | 63.4 | 31.3 | 65.9 | 0.974 |
| D | IPA | BzOH | 3 | 10 | 20 | 140 | 6 | 93.9 | 53.4 | 20.9 | 80.0 | 0.268 |
| III | pyrrolidine | BzOH | 3 | 10 | 13.5 | 80 | 2.8 | 35.9 | 82.9 | 12.0 | 82.7 | 0.336 |
| IV | pyrrolidine | BzOH | 3 | 10 | 13.5 | 110 | 2 | 96.7 | 87.7 | 32.4 | 87.2 | 1.355 |
| E | piperidine | HAc | 2 | 10 | 22 | 110 | 2 | — | — | — | — | —* |
| F | diethylamine | HAc | 2 | 10 | 22 | 110 | 2 | — | — | — | — | —* |

*no product formed
IPA: isopropylamine
BzOH: benzoic acid
HAc: acetic acid
ACN: acrylonitrile
cpton: cyclopentanone
alfa: molar ratio of ketone to nitrile
beta: molar ratio of nitrile to amine
gamma: molar ratio of amine to acid

TABLE 2

| Experiment No. | Ketone | Amine | Acid | alfa | beta | gamma | T (°C.) | t (hours) | conv. ACN (%) | sel. ACN (%) | conv. ketone (%) | sel. ketone (%) | product |
| --- | --- | --- | --- | --- | --- | --- | --- | --- | --- | --- | --- | --- | --- |
| G | chon | pyrrolidone | BzOH | 1.7 | 15 | 7.5 | 130 | 1.5 | — | — | — | —* | CECH |
| H | chon | IPA | BzOH | 1.7 | 15 | 7.5 | 130 | 1.5 | 100 | 85.6 | 58.2 | 86.3 | CECH |
| I | chon | IPA | BzOH | 2 | 20 | 5 | 130 | 1.5 | 95 | 91.8 | 47.3 | 92.1 | CECH |
| J | acetone | pyrrolidine | BzOH | 5 | 12 | 24 | 180 | 4 | 32 | 63 | 10.6 | 37.7 | CHN |
| K | acetone | IPA | BzOH | 5 | 12 | 24 | 180 | 4 | 93 | 79 | 23.3 | 63 | CHN |

*no product formed
ACN: acrylonitrile
chon: cyclohexanone
IPA: isopropylamine
BzOH: benzoic acid
CECH: 2-(2-cyanoethyl)-cyclohexanone
CHN: 5-oxohexane nitrile
alfa: molar ratio of ketone to nitrile
beta: molar ratio of nitrile to amine
gamma: molar ratio of amine to acid

We claim:

1. Method for the preparation of 2-(2-cyanoethyl)-cyclopentanone by reaction of cyclopentanone with $\alpha$, $\beta$-unsaturated nitrile, in the presence of a catalytic amount of amine, characterized in that the amine used is pyrrolidine and the $\alpha$, $\beta$-unsaturated nitrile is selected from the group consisting of acrylonitrile, methacrylonitrile and crotononitrile.

2. Method according to claim 1, characterized in that a catalytic amount of an acid compound is also present in the reaction mixture.

3. Method according to claim 2, characterized in that the acid compound used is acetic acid.

4. Method according to one of claim 1, characterized in that the molar ratio of cyclopentanone to $\alpha$, $\beta$-unsaturated nitrile is between 1.5 and 3.

5. Method according to one of claims 1, characterized in that the reaction is carried out at a temperature of between 80° C. and 150° C.

6. Method according to one of claim 1, characterized in that the reaction is carried out under a pressure of between 0.1 and 2 MPa.

7. A method of preparing 2-(2-cyanoethyl)-cyclopentanone by allowing cyclopentanone to react with an $\alpha$, $\beta$-unsaturated nitrile, in the presence of a catalytic amount of pyrrolidine at a temperature of between 80° C. and 150° C. under a pressure of between 0.1-2 MPa wherein cyclopentanone and $\alpha$, $\beta$-unsaturated nitrile are present at a molar ratio of between 1.5 and 3 and the $\alpha$, $\beta$-unsaturated nitrile is selected from the group consisting of acrylonitrile, methacrylonitrile and crotononitrile.

8. The method according to claim 7, wherein said $\alpha$, $\beta$-unsaturated nitrile is acrylonitrile.

9. The method according to claim 7, wherein said reaction is conducted int he presence of about 0.01-1 mols of an acid compound per mol of pyrrolidine, said acid compound being selected from the group consisting of acetic acid, benzoic acid, caproic acid, hydrochloric acid, phosphoric acid and sulphuric acid.

10. The method according to claim 7, wherein pyrrolidine is present in an amount between 0.05 and 0.2 mol per mol of $\alpha$, $\beta$-unsaturated nitrile.

* * * * *